US012648910B2

(12) United States Patent
Roh et al.

(10) Patent No.: US 12,648,910 B2
(45) Date of Patent: Jun. 9, 2026

(54) LYMPHOMA CELL-SPECIFIC DRUG DELIVERY SYSTEM FOR PREVENTION OR TREATMENT OF LYMPHOMA AND METHOD FOR PREPARING SAME

(71) Applicant: Industry-Academic Cooperation Foundation, Yonsei University, Seoul (KR)

(72) Inventors: Young Hoon Roh, Seoul (KR); Tae Hyung Kim, Seoul (KR); Eun Ji Kwak, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 430 days.

(21) Appl. No.: 17/899,100

(22) Filed: Aug. 30, 2022

(65) Prior Publication Data

US 2023/0086030 A1     Mar. 23, 2023

(30) Foreign Application Priority Data

Aug. 30, 2021     (KR) ........................ 10-2021-0115083
Jan. 20, 2022     (KR) ........................ 10-2022-0008408

(51) Int. Cl.
| | |
|---|---|
| *A61K 9/16* | (2006.01) |
| *A61K 47/36* | (2006.01) |
| *C07K 16/28* | (2006.01) |

(52) U.S. Cl.
CPC ............ *A61K 9/1635* (2013.01); *A61K 47/36* (2013.01); *C07K 16/2803* (2013.01); *C07K 16/2887* (2013.01)

(58) Field of Classification Search
None
See application file for complete search history.

(56) References Cited

FOREIGN PATENT DOCUMENTS

| | | |
|---|---|---|
| KR | 10-2016-0108391 | 9/2016 |
| KR | 10-2017-0134525 | 12/2017 |
| KR | 10-2017-0140377 | 12/2017 |
| KR | 10-2018-0054625 | 5/2018 |

OTHER PUBLICATIONS

Anonymous, Non-Hodgkin Lymphoma, 2024, Lymphoma Research Foundation, https://lymphoma.org/wp-content/uploads/2024/10/Non_Hodgkin_Lymphoma_Fact_Sheet_2024.pdf, accessed Dec. 6, 2024 (Year: 2024).*
Choi, K.Y. et al., Binary targeting of siRNA to hematologic cancer cells in vivo using layer-by-layer nanoparticles, Advanced Functional Materials, 2019, vol. 29, 1900018 (Year: 2019).*

Lopes de Menezes, D.E. et al., In Vitro and in Vivo targeting of immunoliposomal doxorubicin to human B-cell lymphoma, Cancer Research, 1998, vol. 58, 3320-3330 (Year: 1998).*
Kim, T. et al., Dual-targeting RNA nanoparticles for efficient delivery of polymeric siRNA to cancer cells, Chemical Communications, Jun. 21, 2020, vol. 56, 6624 (Year: 2020).*
Honary, S. et al., Effect of zeta potential on the properties of nano-drug delivery systems—A review (Part 1), Tropical Journal of Pharmaceutical Research, 2013, vol. 12, 255-264 (Year: 2013).*
Laginha, K. et al., Liposomes targeted via two different antibodies: Assay, B-cell binding and cytotoxicity, Blochimica et Biophysica Acta, 2005, vol. 1711, 25-32 (Year: 2005).*
Nevala, Wendy K. et al., "Antibody-targeted paclitaxel loaded nanoparticles for the treatment of CD20+ B-cell lymphoma", Scientific Reports, Apr. 2017, 7:45682, 9 pages.
Ho, Benjamin N. et al., "Update on Nanotechnology-based Drug Delivery Systems in Cancer Treatment", Anticancer Research, 2017, vol. 37, pp. 5975-5981.
Choi, Ki Y. et al., "Binary Targeting of siRNA to Hematologic Cancer Cells In Vivo Using Layer-by-Layer Nanoparticles", Advanced Functional Materials, Vo. 29, No. 1900018, 13 pages (2019).
Kim, Taehyung et al., "Dual targeting RNA nanoparticles for efficient delivery of polymeric siRNA to cancer cells", Chemical Communications, DOI: 10.1039/DOCC01848A, 5 pages (2020).
Office Action issued Nov. 24, 2024 in Korean Appln. No. 10-2022-0109121, 5 bpages.
Gu, W., et al., "Polymeric nanomedicines targeting hematological malignancies", Journal of Controlled Release, 2021, vol. 337, pp. 571-588.
Kwak, E., et al., "Polymeric siRNA Nanoparticles for B-cell Lymphoma-specific Delivery by Functionalized Hyaluronic Acid and CD20 Antibody", 2020 KSBB Spring Meeting and International Symposium: e-Conference, Abstract P0908, p. 367.

* cited by examiner

*Primary Examiner* — Bethany P Barham
*Assistant Examiner* — Paul Hoerner
(74) *Attorney, Agent, or Firm* — Wenderoth, Lind & Ponack, L.L.P.

(57) ABSTRACT

Disclosed are a lymphoma cell-specific drug delivery system for the prevention or treatment of lymphoma and a production method therefor. The lymphoma cell-specific drug delivery system may be delivered into lymphoma cells in an improved manner compared to conventional single-target drug delivery systems, and is applicable to the delivery of various therapeutic drugs for the treatment of lymphoma through the application of a wide range of drugs and the same antibody functionalization strategy on the surface of different types of nanoparticles. In addition, the drug delivery system may be introduced into lymphoma as well as other cancer types by adjusting the type and mixing ratio of antibody, and may propose a method of introducing polymeric nucleic acid drugs having superior physiological stability and drug efficacy compared to conventional monomeric nucleic acid drugs, thereby enabling effective drug treatment of lymphoma which is highly resistant to intracellular drug delivery.

7 Claims, 9 Drawing Sheets

Specification includes a Sequence Listing.

A Synthesis of surface-functionalized polymeric siRNA nanoparticle

B Optimal strategy of targeting moieties

C Antibody conjugation via TET-TCO click chemistry

Fig. 2

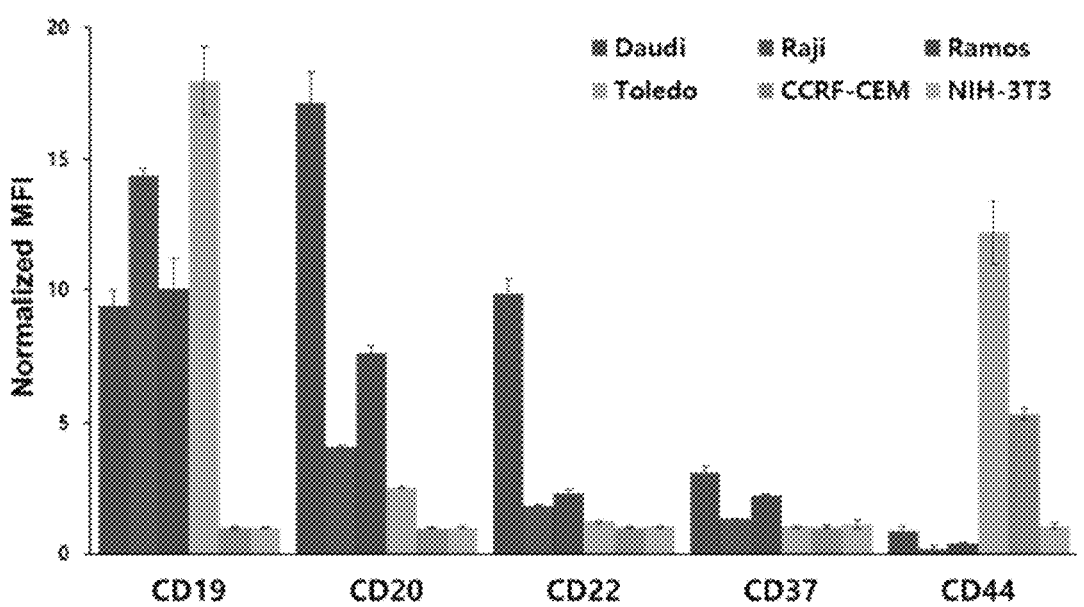

Fig. 3

Table S1. Phosphorylated linear ssDNA and primer ssDNA used for polymeric siRNA microparticle synthesis

| Strand | Sequence |
|---|---|
| Linear ssDNA (Non-specific, NS) | 5'~/5Phos/ATA GTG AGT CGT ATT AAC GTA CCA ACA AGC TGA AAG AAC ACG AAC TTT TAC TTG AAA AGT TCG TGT TCT TTC AGC TTT AGA GGC ATA TCC CT~3' |
| Linear ssDNA (BCL-2 targeting, BCL2) | 5'~/5Phos/ ATA GTG AGT CGT ATT AAC GTA CCA ACA ATG GCA TGA GAT GCA GGA AAT TAC TTG AAT TTC CTG CAT CTC ATG CCA TTT AGA GGC ATA TCC CT~3' |
| Primer ssDNA | 5'~TAA TAC GAC TCA CTA TAG GGA T~3' |

Abbreviations: BCL-2, B-cell lymphoma-2; Phos, phosphorylated; siRNA, small interfering RNA; ssDNA, single-stranded DNA.

Fig. 6

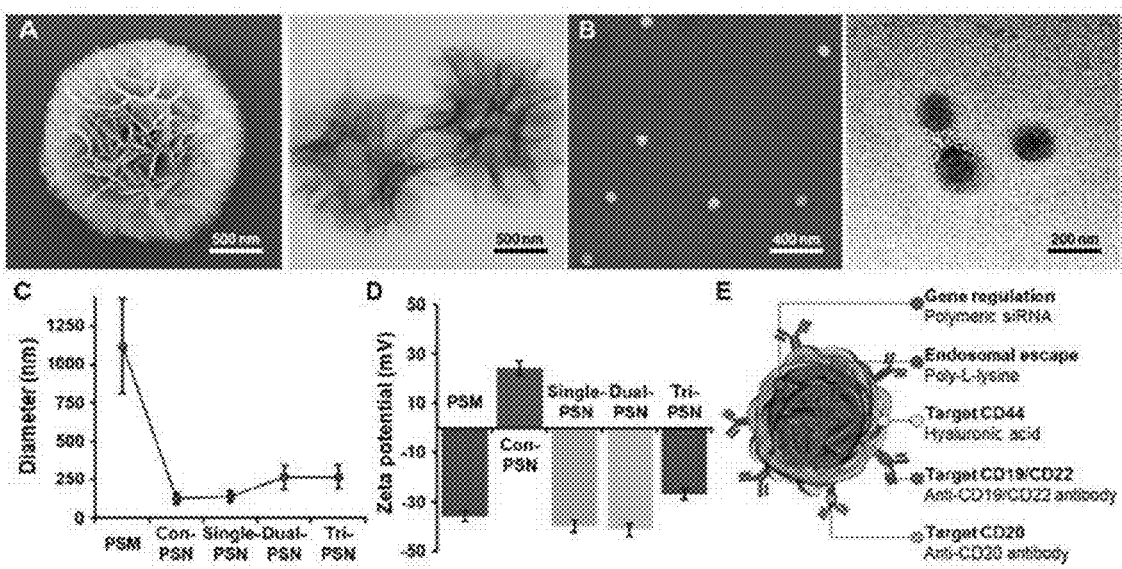

Fig. 7

Table 1. Physicochemical Characterization of Polymeric siRNA particles[a]

| Particle type | Functional biomaterial | Particle size (nm) | PDI | Zeta potential (mV) |
|---|---|---|---|---|
| PSM | siRNA | 1,119.7 ± 309.5 | 1.377 | −35.6 ± 2.2 |
| Con-PSN | PLL | 126.3 ± 36.2 | 0.277 | 24.4 ± 2.7 |
| Single-PSN | HA | 139.8 ± 38.3 | 0.320 | −39.7 ± 2.4 |
| Dual-PSN | Ab/HA | 263.3 ± 75.6 | 0.294 | −41.2 ± 2.4 |
| Tri-PSN | Ab/HA | 267.2 ± 75.2 | 0.287 | −26.8 ± 2.2 |

[a]Abbreviations: Ab, antibody; Dual-PSN, single antibody-conjugated polymeric siRNA nanoparticle; Con-PSN, condensed polymeric siRNA nanoparticles; HA, hyaluronic acid; PDI, polydispersity index; PLL, poly-L-lysine; PSM, polymeric siRNA microparticle; PSN, polymeric siRNA nanoparticle; and Tri-PSN, triple targeting moiety-functionalized polymeric siRNA nanoparticle.

Fig. 8

Table S1. Conjugation efficacy of additive antibody on Dual-PSNs and Tri-PSNs

| Platform | Labelled antibody | Antibody/HA ratio on PSNs (ng/ng) | Conjugation efficacy (%) | Conjugated antibody (ng) |
|---|---|---|---|---|
| Dual-PSNs | α-CD20 | 0.4 | 97.3% | 3.9 |
| | | 0.1 | 21.9% | 0.9 |
| | | 0.2 | 18.1% | 1.4 |
| Tri-PSNs | α-CD19 | 0.4 | 12.7% | 2.0 |
| | | 0.8 | 12.0% | 3.8 |
| | | 1.6 | 8.5% | 5.4 |

Abbreviations: Dual-PSN, single antibody-conjugated polymeric siRNA nanoparticle; Tri-PSNs, triple targeting moiety-functionalized polymeric siRNA nanoparticles.

Fig. 9

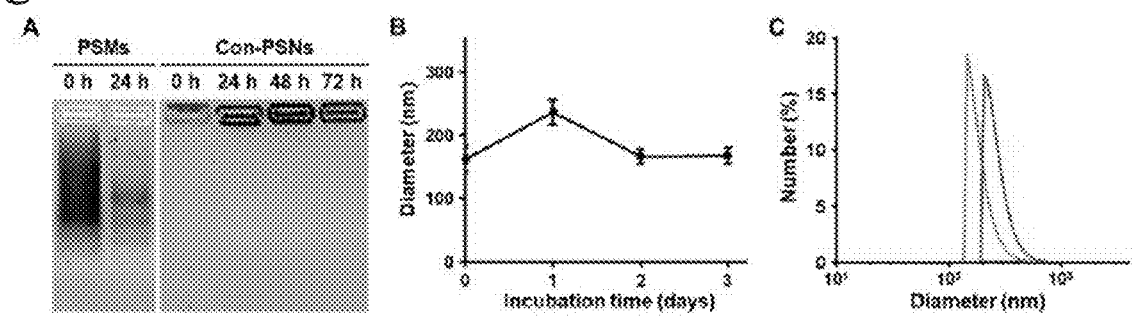

Fig. 15
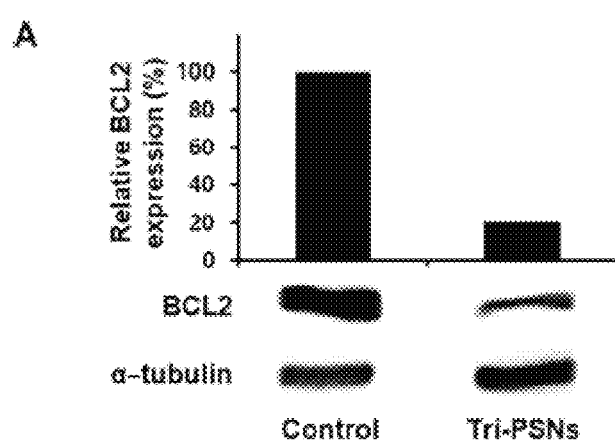
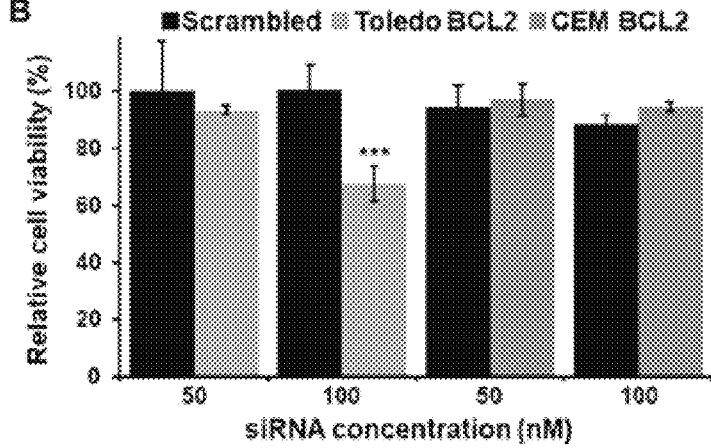

SEQUENCE LISTING

```
Sequence total quantity: 3
SEQ ID NO: 1            moltype = DNA   length = 92
FEATURE                Location/Qualifiers
source                 1..92
                       mol_type = other DNA
                       organism = synthetic construct
SEQUENCE: 1
atagtgagtc gtattaacgt accaacaagc tgaaagaaca cgaactttta cttgaaaagt   60
tcgtgttctt tcagctttag aggcatatcc ct                                 92

SEQ ID NO: 2            moltype = DNA   length = 92
FEATURE                Location/Qualifiers
source                 1..92
                       mol_type = other DNA
                       organism = synthetic construct
SEQUENCE: 2
atagtgagtc gtattaacgt accaacaatg gcatgagatg caggaaatta cttgaatttc   60
ctgcatctca tgccatttag aggcatatcc ct                                 92

SEQ ID NO: 3            moltype = DNA   length = 22
FEATURE                Location/Qualifiers
source                 1..22
                       mol_type = other DNA
                       organism = synthetic construct
SEQUENCE: 3
taatacgact cactataggg at                                            22
```

1

LYMPHOMA CELL-SPECIFIC DRUG DELIVERY SYSTEM FOR PREVENTION OR TREATMENT OF LYMPHOMA AND METHOD FOR PREPARING SAME

SEQUENCE LISTING

A sequence listing in electronic (XML file) format is filed with this application and incorporated herein by reference. The name of the ASCII text file is "2022-1741A. xml"; the file was created on Oct. 17, 2022; the size of the file is 3,920 bytes.

BACKGROUND

1. Technical Field

The present disclosure relates to a lymphoma cell-specific drug delivery system for the prevention or treatment of lymphoma and a method for producing the same.

2. Related Art

RNA interference (RNAi) therapeutics, such as small interfering RNAs (siRNAs), have been highlighted as powerful cancer therapeutics due to their specific and effective disease-related gene regulation potential. However, their clinical applications are still limited due to intravascular degradation, lack of tissue penetrance, intracellular delivery, and nonspecific delivery. To overcome these limitations, various siRNA nanodelivery platforms have been developed using RNA nanotechnology. In particular, polymeric siR-NAs synthesized using rolling circle transcription (RCT) have attracted extensive attention owing to their enhanced structural stability, increased payloads, and high gene silencing efficacy. Recently, this platform has been further developed by employing suitable functional nanomaterials to facilitate tissue penetration, intracellular delivery, and ensure enhanced pharmacokinetics, and by adopting active targeting agents including antibodies, aptamers, and polysaccharides to enable tumor-specific polymeric siRNA delivery.

To address the delivery challenges associated with polymeric siRNA nanoparticles, we previously reported an actively targeted particle strategy that allowed the engineering of nanoparticles with two different targeting moieties to finely tune and control targetability for adherent cancer cells.

Hematologic malignancies, including leukemia, lymphoma, and myeloma, have presented clinical challenges due to the difficulty of targeted drug delivery. Especially, non-Hodgkin's lymphoma (NHL) is one of the most prevalent hematologic cancers and prevailing lymphoid malignancies worldwide, occurs in a hard-to-transfect disease site. In South Korea, non-Hodgkin's lymphoma (NHL) accounts for more than 90% of lymphomas occurring in Korea, and ranks among the top 10 cancers in both males and females in terms of mortality.

Many of the common types of aggressive NHL have been treated with standard chemotherapy regimens comprising cyclophosphamide, hydroxydaunorubicin, oncovin, and prednisone. In addition, rituximab, a chimeric anti-CD20 human monoclonal antibody, has become the standard treatment for NHL along with standard chemotherapy. However, resistance to rituximab through antibody effector mechanisms (antibody-dependent cellular cytotoxicity, complement-dependent cytotoxicity, and apoptosis), Fc-receptor polymorphisms, and downregulation or loss of CD20 expression in lymphoma cells has been reported.

Functionalizing targeting moieties by engineering the surface chemistry is key to successfully designing targeted drug delivery platforms that minimize possible nonspecific interactions, which cause side effects to healthy cells and induce substantial accumulation of the therapeutic agents in diseased cells. Thus, such platforms deliver nanomedicines more efficiently. In general, the nanoparticle surface is coupled with one or more targeting moieties (e.g., antibodies or their fragments, aptamers, or receptor ligands including peptides, vitamins, and carbohydrates) for efficient delivery of encapsulated drugs.

As a powerful nanoengineering approach for NHL therapy, several antibodies (anti-CD20 or anti-CD38) have recently been employed as a targeting moiety on the nanoparticle surface. However, single-ligand-conjugated platforms are insufficient to target particular lymphoma cells and may induce receptor saturation, consequently leading to low receptor-mediated endocytosis.

In this context, dual-targeted delivery platforms of the present disclosure have been designed for specific delivery of therapeutics to lymphoma cells by adapting additional targeting moieties. For example, hyaluronic acid (HA; CD44 receptor ligand) or the anti-CD37 antibody was coupled to the anti-CD20 antibody, wherein each nanoplatform (immunoliposome, a layer-by-layer nanoparticle) showed improved biodistribution and circulating behavior with substantial targetability and enhanced internalization than single targeted platforms. Their therapeutic efficacy was also validated in vitro and in vivo. Despite these trials, specific multiple biomarkers of NHL still need to be investigated for a broad range of disease-specific delivery. Moreover, the presence of circulating NHL cells in the blood and the low efficacy of conventional transfection methods have imposed additional biological barriers for delivery of therapeutics.

PRIOR ART DOCUMENTS

Patent Documents (Patent Document 1) KR 10-2019-0030452A

SUMMARY

The present disclosure has been made in order to solve the above-described problems, and an object of the present disclosure is to provide a non-Hodgkin's lymphoma cell-specific drug delivery system and a method for producing the same.

According to one aspect of the present disclosure, there is provided a lymphoma cell-specific drug delivery system for the prevention or treatment of lymphoma, the drug delivery system being composed of a nanoparticle including: a core containing a concentrated mixture of a prophylactic or therapeutic drug and poly-L-lysine; a shell composed of hyaluronic acid layered on the surface of the core; an anti-CD20 antibody conjugated to the surface of the shell; and an anti-CD19 antibody or anti-CD22 antibody conjugated to the surface of the shell.

According to another aspect of the present disclosure, there is provided a method for producing the drug delivery system.

Antibody-functionalized nanoparticles for non-Hodgkin's lymphoma cell-specific drug delivery according to the present disclosure may be delivered into lymphoma cells in an improved manner compared to conventional single-target drug delivery systems, and are applicable to the delivery of various therapeutic drugs for the treatment of non-Hodgkin's lymphoma through the application of a wide range of drugs and the same antibody functionalization strategy on the surface of different types of nanoparticles. In addition, the antibody-functionalized nanoparticles according to the present disclosure may be introduced into lymphoma as well as other cancer types by adjusting the type and mixing ratio of antibody, and may propose a method of introducing polymeric nucleic acid drugs having superior physiological stability and drug efficacy compared to conventional monomeric nucleic acid drugs, thereby enabling effective drug treatment of non-Hodgkin's lymphoma which is highly resistant to intracellular drug delivery.

BRIEF DESCRIPTION OF THE DRAWINGS

FIG. 2 shows the results of flow cytometry analysis of Daudi, Raji, Ramos, Toledo, CCRF-CEM, and NIH-3T3 cells after CD19-, CD20-, CD22-, CD37-, and CD44-targeted immunostaining.

FIG. 3 shows phosphorylated linear SSDNAS (Non-specific: SEQ ID NO: 1; BCL-2 targeting: SEQ ID NO: 2) and primer ssDNA (SEQ ID NO: 3) used for polymeric siRNA microparticle synthesis.

FIG. 6 shows morphological and structural characterization of (A) PSMs and (B) Tri-PSNs by SEM and TEM; (C) size and (D) surface charge of the polymeric siRNA particles during each synthesis process; and (E) schematic illustration of each functional component of the Tri-PSNs.

FIG. 7 shows the results of physicochemical characterization of polymeric siRNA particles.

FIG. 8 shows the conjugation efficacy of additive antibody on Dual-PSNs and Tri-PSNs.

FIG. 9 shows biostability of Tri-PSNs. (A) Electrophoretic analysis of polymeric siRNA in PSMs and Con-PSNs after serum incubation at the indicated time points; (B) hydrodynamic size of Tri-PSNs upon incubation with a 10% FBS solution for up to 3 days; and (C) size distribution of Tri-PSNs at different pH environments.

FIG. 15 shows in vitro therapeutic efficacy of Tri-PSNs. (A) Western blot and densitometric analysis of BCL2 levels in Tri-PSNs-treated Toledo cells; and (B) cell viability of Tri-PSNs-treated Toledo and CEM cells with different concentrations of BCL2 polymeric siRNA.

DETAILED DESCRIPTION

Figure 1:
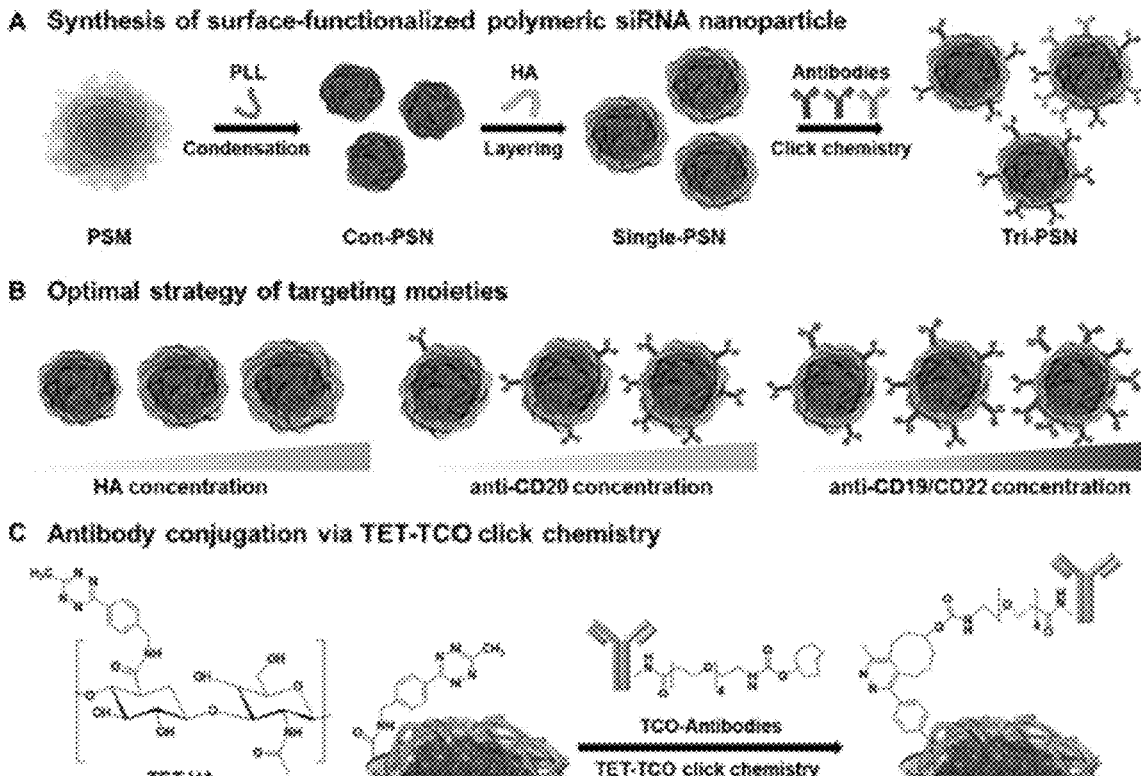
FIG. 1 is a schematic illustration of nanoparticle synthesis. (A) Three synthesis procedures of surface-functionalized PSNs: condensation, HA layering, and antibody conjugation; (B) optimization of conjugation ratio of targeting moieties; and (C) conjugation of antibody-TCO to HA-TET-layered PSNs.

The present disclosure will be described in detail as follows. Meanwhile, each description and embodiment disclosed in the present disclosure may be applied to each other description and embodiment. That is, all combinations of the various elements disclosed in the present disclosure fall within the scope of the present disclosure. In addition, the scope of the present disclosure is not construed as being limited by the specific embodiments described below.

One aspect of the present disclosure for achieving the above-described object provides a lymphoma cell-specific drug delivery system for the prevention or treatment of lymphoma, the drug delivery system being composed of a nanoparticle including: a core containing a concentrated mixture of a prophylactic or therapeutic drug and poly-L-lysine; a shell composed of hyaluronic acid layered on the surface of the core; an anti-CD20 antibody conjugated to the surface of the shell; and an anti-CD19 antibody or anti-CD22 antibody conjugated to the surface of the shell.

The present disclosure is directed to Tri-PSNs designed and developed to target NHL cells using three types of targeting moieties: a natural ligand, that is, hyaluronic acid that is an NHL-specific targeting moiety targeting the CD44 receptor, and two additional combinations of antibodies. This nanoplatform of the present disclosure may be specifically and intracellularly delivered to various human NHL cell lines and consequently, may inhibit the proliferation of these cells by regulating the expression of the targeted gene (e.g., BCL2) through RNAi therapeutics. Thus, the application of Tri-PSNs of the present disclosure may provide in vivo anticancer effects, biodistribution and nonspecific accumulation, and predictive targetability. In addition, the drug delivery platform of the present disclosure, in combination with RNAi therapeutics targeting oncogenes and chemotherapy regimens, may potentially inhibit cancer growth, thereby demonstrating the applicability of siRNA nanoplatforms to other hematological malignancies through the combination of cell-targeting moieties.

In the present disclosure, the poly-L-lysine is a substance produced by chain growth polymerization of the amino acid lysine. The poly-L-lysine increases positively charged sites capable of binding to cells, thereby increasing the electrostatic attraction between negatively charged ions of the cell membrane and positively charged ions of the outer surface.

In the present disclosure, the prophylactic or therapeutic drug may be at least one of various nucleic acid drugs, including siRNA, mRNA, miRNA, anti-sense ODN, viral vectors, and plasmids, or polymeric forms thereof. More specifically, the prophylactic or therapeutic drug may be an anticancer drug, an anticancer adjuvant agent, or an siRNA that inhibits the expression of a target gene in lymphoma cells. Specifically, the prophylactic or therapeutic drug may be an siRNA that inhibits the expression of a target gene in lymphoma cells. More specifically, it may be an siRNA that inhibits the expression of BCL2 gene, without being limited thereto.

In the present disclosure, the target gene in lymphoma cells may be BCL2 gene, but is not limited thereto and may also be any gene related to inhibition of the proliferation, expression and metastasis of lymphoma cells.

In the present disclosure, the lymphoma may be Burkitt's lymphoma, diffuse large B-cell lymphoma (DLBCL), Hodgkin's lymphoma, or non-Hodgkin's lymphoma, and more specifically, may be non-Hodgkin's lymphoma.

In the present disclosure, the weight ratio of the anti-CD20 antibody to the hyaluronic acid in the nanoparticle may be 0.3 to 0.5, specifically 0.4. The weight ratio of the anti-CD19 antibody to the hyaluronic acid in the nanoparticle may be 0.05 to 0.15, specifically 0.1. This weight ratio of each antibody to the hyaluronic acid is related to the efficiency of antibody conjugation, and if the weight ratio of each antibody to the hyaluronic acid is out of the above range, a problem may arise in that the efficiency with which the antibody is conjugated to the nanoparticle is lowered.

In the present disclosure, the drug delivery nanoparticle or delivery system may have a diameter of 250 to 270 nm, and the zeta potential of the drug delivery nanoparticle or delivery system may be in the range of −25 to −27 mV. In addition, the drug delivery nanoparticle or delivery system may have a zeta-potential of −20 to −22 mV in an environment of pH 6.3 to 6.5. Thereby, the nanostructure may maintain optimal conditions for cell interaction in an environment of pH 6.3 to 6.5, which is a tumor tissue microenvironment.

In the present disclosure, regarding the weight ratio of each antibody to the hyaluronic acid (HA) in the drug delivery nanoparticle or delivery system, the anti-CD20 antibody and HA may be included at a weight ratio of 0.3 to 1.0, 0.3 to 0.9, 0.35 to 0.85, or 0.4 to 0.8, the anti-CD22 antibody and HA may be included at a weight ratio of 1.5 to 1.7, or 1.6, and the anti-CD19 antibody and HA may be included at a weight ratio of 0.3 to 1.0, 0.3 to 0.9, 0.35 to 0.85, or 0.4 to 0.8. This weight ratio is critical to optimization of surface ligand density on the nanoparticle, and this weight ratio of each antibody to the hyaluronic acid is greatly significant in that the surface ligand density is highly important for efficient targeted cell delivery.

Another aspect of the present disclosure provides a method for producing the lymphoma cell-specific drug delivery system. Specifically, the method includes steps of: synthesizing an siRNA that complementarily binds to a target gene in lymphoma cells; synthesizing polymeric siRNA microparticles by mixing and incubating a ribonucleotide solution containing the siRNA, a buffer, a reducing agent, and a polymerase; synthesizing concentrated polymeric siRNA nanoparticles by mixing a fluorophore-conjugated poly-L-lysine solution, a buffer, and the polymeric siRNA microparticles; synthesizing hyaluronic acid-layered polymeric siRNA nanoparticles by mixing and incubating the concentrated polymeric siRNA nanoparticles with a hyaluronic acid solution and a tetrazine solution; and adding a trans-cyclooctene-NHS ester (TCO)-conjugated antibody to the hyaluronic acid-layered polymeric siRNA nanoparticles, thereby conjugating the antibody to the surfaces of the nanoparticles.

In the present disclosure, the contents regarding the above-described drug delivery system are equally applied to each step and configuration of the production method.

In the present disclosure, the surface charge of the polymeric siRNA nanoparticles may be changed within a range of −35 to 45 mV through hyaluronic acid layering in the production method. Thereby, it is possible to prevent the drug delivery system from being delivered to non-target cells.

In the present disclosure, the hyaluronic acid solution may be added at a concentration of 0.3 to 0.5 mg/ml, specifically 0.4 mg/ml, which is related to optimization of surface ligand density on the nanoparticles.

Still another aspect of the present disclosure provides a method of inhibiting proliferation or survival of lymphoma cells in vitro. Specifically, the method includes steps of: producing the drug delivery system through the above-described production method; and administering the produced drug delivery system to lymphoma cells in vitro.

In the present disclosure, the contents regarding the above-described drug delivery system and production method are equally applied to each step and configuration of the inhibition method.

Hereinafter, the present disclosure will be described in more detail with reference to examples. However, these examples are for illustratively describing the present disclosure, and the scope of the present disclosure is not limited to these examples.

Example 1: Experimental Methods

1.1. Synthesis of Polymeric siRNA Microparticles and Nanoparticles

To synthesize circular DNA, a phosphorylated linear single-stranded DNA (SSDNA) (SEQ ID NO: 1), including the sequence complementary to the siRNA targeting BCL2 (92 bp) (SEQ ID NO: 2) and an ssDNA including the T7 promoter sequence (22 bp) (SEQ ID NO: 3), were designed. For hybridization, 1 UM of each of the two DNA strands was mixed, heated at 95° C. for 2 min, and gradually cooled down to 20° C. in a T100 Thermal Cycler (Bio-Rad Laboratories, Hercules, CA, USA). The hybridized DNA was then ligated by T4 ligase (0.03 U/μL) in ligase buffer (300 mM Tris-HCl, 100 mM $MgCl_2$, 10 mMATP, and 100 mM DTT, pH 7.8) at 24° C. for 24 h. Electrophoresis was performed using a 3% agarose gel prestained with GelRed in 1× TBE buffer and run at 80 V for 60 min to observe the formation of the circular DNA. Its image was obtained with a gel documentation system (Gel Doc XR+; Bio-Rad Laboratories), and it was quantified using ImageJ v1.8 software (National Institutes of Health, Bethesda, MD, USA).

Polymeric siRNA microparticles (PSMs) were synthesized by incubating the circular DNA (0.3 UM) with a ribonucleotide solution mix (2.5 mM), DTT (6 mM), and T7 polymerase (20 U/μL) in a reaction buffer (40 mM Tris-HCl, 6 mM $MgCl_2$, 1 mM DTT, and 2 mM spermidine, pH 7.9). This mixture was incubated at 37° C. for 16 h, pipetted and sonicated to obtain monodisperse particles, and centrifuged at 3,000×g for 5 min. The supernatants were removed and the pellet was resuspended in nuclease-free water.

Before synthesizing the condensed (con)-PSN, we prepared a Cy5.5-conjugated poly-L-lysine (PLL) solution. Briefly, PLL (30-70 kDa, 10 mg/mL) was mixed with Cy5.5 and incubated for 12 h at 24° C. to obtain a Cy5.5-conjugated PLL solution.

Next, 1 M $K_2HPO_4$ and EtOH were added to concentrate the mixture, and unconjugated PLL and Cy5.5 were removed by centrifugation at 12,100×g for 5 min, after which the supernatant was removed. The collected pellet was resuspended in EtOH, centrifuged again as described above, and resuspended in 0.01 N HCl. The Cy5.5-conjugated PLL solution was added to the PSM solution at 2 mg/mL in Tris buffer (10 mM Tris and 150 mM NaCl, pH 4.0) and reacted on an orbital shaker for 12 h at 24° C. Unreacted Cy5.5-conjugated PLL molecules were removed by centrifugation at 12,100×g for 5 min and the supernatant was discarded.

For HA layering, Con-PSNs were resuspended in 100 nM phosphate buffered saline (pH 7.4); tetrazine (TET) functionalized with the HA stock solution (200 kDa, 10 mg/mL) was mixed with the Con-PSN solution at 0.4 mg/mL, followed by incubation for 12 h at 24° C. Unreacted HA was removed by centrifugation at 12,100×g for 5 min and the supernatant was discarded.

To conjugate the antibodies onto single ligand-modified PSNs (Single-PSNs), the trans-cyclooctene-NHS ester (TCO)-conjugated antibody was added to the Single-PSN solution and gently mixed for 12 h at 24° C. Unreacted antibody was removed by centrifugation at 12, 100×g for 5 min. After removing the supernatant, the pellet was resuspended in 40% phosphate buffer (v/v).

1.2. Characterization of the Polymeric siRNA Nanoparticles

To analyze the morphologies of the PSMs, Con-PSNs, Single-PSNs, single antibody-conjugated PSNs (Dual-PSNs), and Tri-PSNs, 10 μL of the sample was placed on a silicon chip substrate (5×5 $mm^2$) (Structure Probe, West Chester, PA, USA) and then dried in an incubator for 2 h. The surface of the PSMs was examined at a voltage of 15 kV, whereas other samples were examined at a voltage of 5 kV using an IT-500 HR field emission scanning electron microscope (JEOL, Tokyo, Japan). To investigate the internal structures of the PSMS, transmission electron microscopy (TEM; JEM-F200, JEOL) was performed in scanning the TEM mode at a voltage of 200 kV. For TEM observation, PSMs were dried on a carbon/formvar-coated TEM grid (200 mesh; Electron Microscopy Sciences, Hatfield, PA, USA).

The size distribution and surface charge of the PSMs and PSNs were evaluated by dynamic light scattering (DLS) and electrophoretic light scattering (ELS), respectively, using an ELS-1000ZS (Otsuka Electronics Co., Osaka, Japan). The particles were dispersed in nuclease-free water and measured at 24° C. To evaluate the antibody conjugation efficiency, the ultraviolet-visible absorbance of the Tri-PSNs before/after conjugating the antibody was calculated for the FITC spectra using a NanoDrop 1000 spectrophotometer (Thermo Fisher Scientific, Waltham, MA, USA) as follows:

$$\text{Antibody conjugation efficiency(\%)} = \left( \frac{Ab_{before} - Ab_{after}}{Ab_{before}} \right) \times 100$$

2.3. Cell Culture

The CCRF-CEM and NIH-3T3 cell lines were provided by the Korean Cell Line Bank (Seoul, South Korea). The B lymphocyte cell lines Daudi, Raji, Ramos, and Toledo were purchased from the American Type Culture Collection (Manassas, VA, USA). Dimethylsulfoxide was purchased from Sigma-Aldrich (St. Louis, MO, USA). All the NHL cell lines and CCRF-CEM cells were cultured in RPMI 1640 medium (Thermo Fisher Scientific) supplemented with 10% (v/v) non-inactivated fetal bovine serum (FBS) and a 1% (v/v) penicillin-streptomycin solution (Corning, Corning, NY, USA). In addition, the NIH-3T3 cells were cultured in Dulbecco's modified Eagle medium (Corning) supplemented with 10% (v/v) bovine calf serum (Thermo Fisher Scientific) and a 1% (v/v) penicillin-streptomycin solution. All the cell lines were incubated at 37° C. in a humidified incubator with 5% $CO_2$.

1.4. In Vitro Cellular Uptake Analysis

To select the targeting moiety ratio of the Tri-PSNs for each B cell line, the cellular uptake rate was measured by flow cytometry and confocal laser scanning microscopy (CLSM). For flow cytometry analysis, PSMs, PSNs, TPSNs, and Tri-PSNs loaded with an siRNA concentration of 20 nM were incubated with 5×10⁴ cells/well in 96-well plates for 4 h at 37° C. and examined using a spectral analyzer. A total of 10,000 events were recorded, and the data were analyzed using SA3800 Spectral Cell Analyzer software (Sony Biotechnology, San Jose, CA, USA). For CLSM analysis, Tri-PSNs with an siRNA concentration of 20 nM were incubated with 5×10⁴ cells/well in 96-well plates for 4 h at 37° C. Following centrifugation at 200×g for 3 min, the cells were fixed with a 10% formalin solution and then stained with 2 μM Hoechst 33342 for 5 min at 24° C. protected from light. The cells were placed onto microscope slides (Fisherbrand Superfrost Plus Microscope Slides; Thermo Fisher Scientific) and covered with a cover glass (Paul Marienfeld GmbH & Co. KG, Lauda-Königshofen, Germany). Cellular uptake of the Tri-PSNs was confirmed using an LSM 700 microscope and the data were analyzed using ZEN software (Carl Zeiss, Oberkochen, Germany).

1.5. In Vitro Therapeutic Efficacy Analysis

To analyze the in vitro therapeutic efficacy of Tri-PSNs, antiproliferative effects by cell viability and gene-silencing effects by western blotting were analyzed. Cell viability following the Tri-PSN treatment was evaluated using alamarBlue. Briefly, the cells were seeded onto 96-well plates at a density of 1×10⁴ cells/well and were then treated with Tri-PSNs with various siRNA concentrations. After 72 h of incubation at 37° C., 10 μL of alamarBlue was added to each well and incubated for 2 h at 37° C. Absorbance was detected at 570 and 600 nm using a microplate reader (Victor X5; PerkinElmer, Waltham, MA, USA). Relative cell viabilities were calculated using that of untreated cells as a reference. For western blotting, all the cells were seeded on 24-well culture plates at a density of 10×10⁴ cells/well and incubated for 24 h at 37° C. The cells were treated with Tri-PSNs loaded with 140 nM siRNA for 72 h at 37° C. The cells were lysed in 100 μL of ice-cold lysis buffer and centrifuged at 16,000×g for 30 min. Western blotting analysis was performed with 20 μg of proteins using anti-BCL2 or anti-α-tubulin antibodies. Images of the membranes were obtained using a gel documentation system (Gel Doc XR+; Bio-Rad Laboratories). The densitometric quantification of the protein bands was performed using ImageJ v1.8 software.

1.6. Statistical Analysis

Experimental data are expressed as the mean±standard deviation (SD) of three samples in each group. Differences between groups were analyzed by one-way analysis of variance with a Scheffe test using the SPSS 25.0 software package (IBM Corp., Armonk, NY, USA). Statistical significance is represented as *p<0.05,  p<0.01, and * p<0.001.

Example 2: Experimental Results

2.1. Selection t Receptors for Surface Engineering

The selection of highly expressed receptors is essential for enhancing the targeting ability and receptor-mediated cellular uptake of nanocarriers. CD19, CD20, CD22, and CD37 receptors have been mainly used as B cell biomarkers, whereas CD44 has been reported to be overexpressed in diffuse large B cell lymphoma (DLBCL). The levels of these receptors were investigated in representative human NHL cell lines Daudi, Raji, and Ramos (Burkitt lymphoma) and Toledo (DLBCL) □y flow cytometry using fluorescence-labeled antibodies (FIG. 2). According to the quantitative flow cytometry analysis, mean fluorescence intensities (MFIs) specific to anti-CD20 and anti-CD19 were significantly higher in the four NHL cell lines than in NIH-3T3, a normal fibroblast cell line, and CCRF-CEM, a lymphocytic leukemia cell line. Among all the receptors, CD20 and CD22 had the highest expression in Daudi cells.

In addition, Raji and Ramos cells showed higher expression of CD19 and CD20 than CCRF-CEM and NIH-3T3 cells. CD19, CD20, and CD44 expression were significantly higher in Toledo than in NIH-3T3 cells. These results indicate that CD20 is an appropriate target receptor for general NHL-specific delivery. CD22 was additionally selected for targeting Daudi cells, whereas CD19 was chosen for Raji and Ramos cell lines. In this context, the Tri-PSN was designed to incorporate HA, a well-known natural ligand of the CD44 receptor, along with the anti-CD20 antibody and an additional anti-CD19/anti-CD22 antibody as an NHL-specific targeting moiety of PSNs.

2.2. Synthesis of Triple Targeting Polymeric siRNA Nanoparticles

Figure 4:
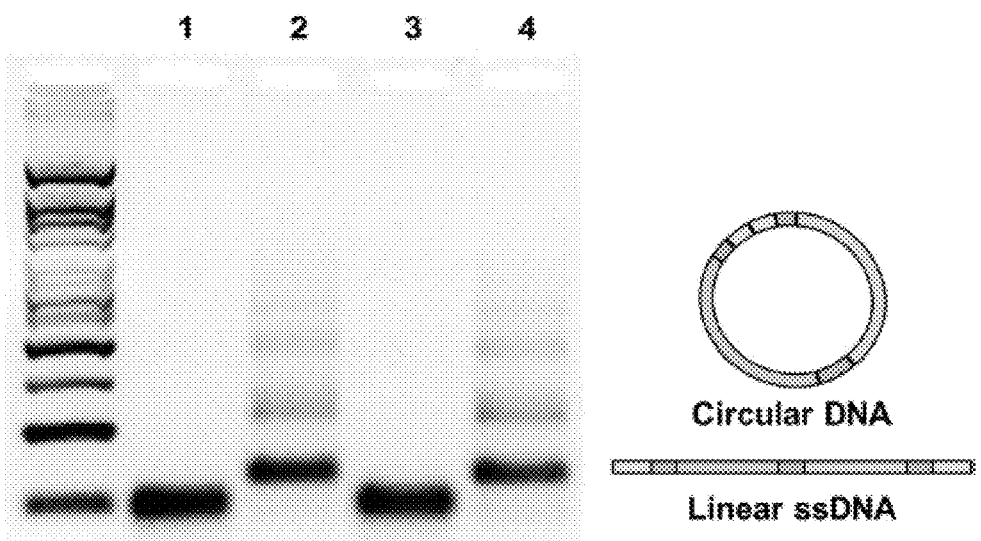
FIG. 4 shows the results of electrophoretic analysis of linear and circular DNAs. Lane 1: linear single-stranded DNA (ssDNA) of a nonspecific (NS) sequence; Lane 2: circular DNA of NS; Lane 3: linear ssDNA of BCL2; Lane 4: circular DNA of BCL2. A band shift was observed when the circular DNA was formed from linear ssDNA.

First, a circular DNA template encoding the sense and antisense strands of BCL2 siRNA therapeutic was designed to fabricate polymeric siRNA (FIG. 3). The synthesis of the circular DNA was confirmed by gel electrophoresis (FIG. 4). A distinct upward-shifted band of the circular DNA, which was heavier than the linear DNA, was observed. Thus, it was verified that the circular DNA was synthesized at over 90% turnover. Based on the circular template, PSMs comprising self-assembled polymeric siRNAs and magnesium pyrophosphate crystal structures were produced via RCT. These anionic microparticles were further condensed with cationic PLL to obtain nanorange sized particles, which are favorable for intracellular delivery and to invert the surface charge for further modification.

Figure 5:
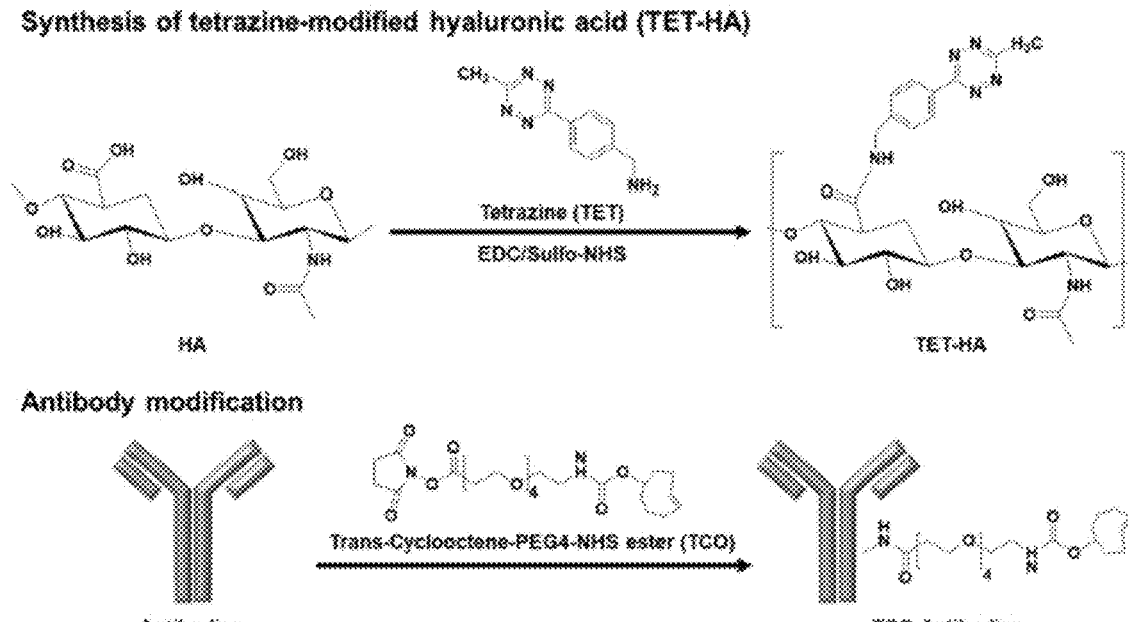
FIG. 5 is a schematic illustration of the process of tetrazine (TET) modification of hyaluronic acid (HA) and modification of antibody by trans-cyclooctene-NHS ester (TCO).

In addition, TET-conjugated HA was electrostatically deposited onto the positively charged Con-PSNs using an intrinsic negative charge, thereby producing Single-PSNs. Finally, the combinations of two TCO-modified antibodies, which were selected from the aforementioned immunostaining results, were conjugated with TET of the deposited HA on the surface of the Single-PSNs via TET-TCO click chemistry, resulting in the synthesis of Tri-PSNs (FIG. 5). Tri-PSNs were then applied for drug delivery to different types of NHL cells.

2.3. Characterization of Polymeric siRNA Microparticles and Nanoparticles

Morphological and structural analyses by scanning electron microscopy (SEM) and TEM revealed the crystalline petal-like structure of the PSMs, which was similar to those reported in previous studies (FIG. 6A). In contrast, Tri-PSNs had spherical morphologies with densely packed and decrystallized structures (FIG. 6B). In addition, given the importance of the size and surface charge for the endocytic mechanism of nanoparticles, the hydrodynamic size and zeta ($\zeta$)-potential of the polymeric RNA particles were analyzed at each synthesis step by DLS and ELS, respectively (FIGS. 6C, 6D and 7).

PSMs showed a microsize of 1,119.7±309.5 nm and anionic properties of −35.6±2.2 mV. The size of the PSMs was additionally reduced by approximately 10-fold through condensation to 126.3±36.2 nm, and their surface charge was converted to 21.0±1.2 mV.

When HA was layered, the surface charge of Con-PSNs changed to −39.7±2.4 mV, and the size of Single-PSNs slightly increased to 139.8±38.3 nm.

After antibody conjugation, the diameter of the nanoparticle increased to 263.3±75.6 nm in the presence of the anti-CD20 antibody. No significant size difference was observed between Tri-PSNs and Dual-PSNs (267.2±75.2). The $\zeta$-potential slightly decreased to −26.8±2.2 mV following the conjugation of two types of antibodies (Tri-PSNs), and the Dual-PSNs showed high negative Z-potentials (−41.2±2.4 mV). Combined with the polydispersity index (PDI) of all the PSNs, these findings demonstrate the successful surface functionalization of multiple targeting moieties.

To further confirm the surface decoration of antibodies by click chemistry, the sequential antibody conjugation efficiency was determined by tracking unconjugated antibodies after labeling with anti-CD19 or anti-CD20 antibodies with a fluorescence dye (FIG. 8). In detail, the conjugation efficiency of the anti-CD20 antibody was 97.3% at 0.4 anti-CD20/HA mass, indicating optimal intracellular delivery. In addition, the anti-CD19 antibody conjugation efficiency on Tri-PSNs was 21.9% at 0.1 anti-CD19/HA mass, which was reduced to 8.5% at 1.6 anti-CD19/HA mass. These results suggest that the conjugation efficiency of the anti-CD19 antibody was limited due to the preceding conjugation of the anti-CD20 antibody, thus indicating the successful conjugation of the two antibodies.

Tri-PSNs with multiple targeting moieties were ultimately developed by a combination of polymeric siRNA for gene regulation, PLL for endosomal escape, HA for targeting the CD44 receptor, and the anti-CD19/CD20 antibody for targeting the CD19 or CD20 NHL receptor, respectively (FIG. 6E).

2.4. Biostability of Polymeric siRNA Nanoparticles

For effective targeted drug delivery applications, it is critical that the polymeric RNA loaded into the nanocarrier is protected and structurally stable under physiological conditions. Therefore, the biostability of the Tri-PSNs was evaluated next.

The polymeric RNA in PSMs and Con-PSNs was incubated in a 10% serum condition and analyzed by electrophoresis to determine the remaining polymeric RNA after serum exposure (FIG. 9A). A considerable amount of polymeric siRNA in the PSMs was depolymerized and degraded within 24 h; however, the polymeric siRNA in Con-PSNs was fully protected during 72 h. The improved stability of the Con-PSNs may be explained by their polyelectrolyte complexation.

Furthermore, Tri-PSNs were incubated in a 10% serum condition for 72 h, and the hydrodynamic size of the particles was analyzed by DLS (FIG. 9B). The hydrodynamic size of the Tri-PSNs was not significantly altered in the presence of serum until 72 h, which indicates their biostability and suitability for interaction with NHL cells.

Lastly, the hydrodynamic size and the Z-potential of the Tri-PSNs at different Ph values (pH 6.4 and 7.0, which mimicked the normal and tumor tissue microenvironments, respectively) were analyzed by DLS and ELS (FIG. 9C). Although the hydrodynamic size of the Tri-PSNs was slightly decreased, their ζ-potential slightly decreased from −24.7÷0.8 to −21.5±1.4 mV at pH 6.4, which implies that the nanostructure of the Tri-PSNs was still maintained for cell interaction in the tumor microenvironment.

2.5. Optimization of Surface Ligand Density on the Nanoparticles

Moreover, as surface ligand density is highly important for efficient targeted cellular delivery, Cy5.5-labeled Tri-PSNs were systematically synthesized with various HA concentrations, anti-CD20 antibody densities per HA, and mass ratios of anti-CD19/anti-CD22.

Figure 10:
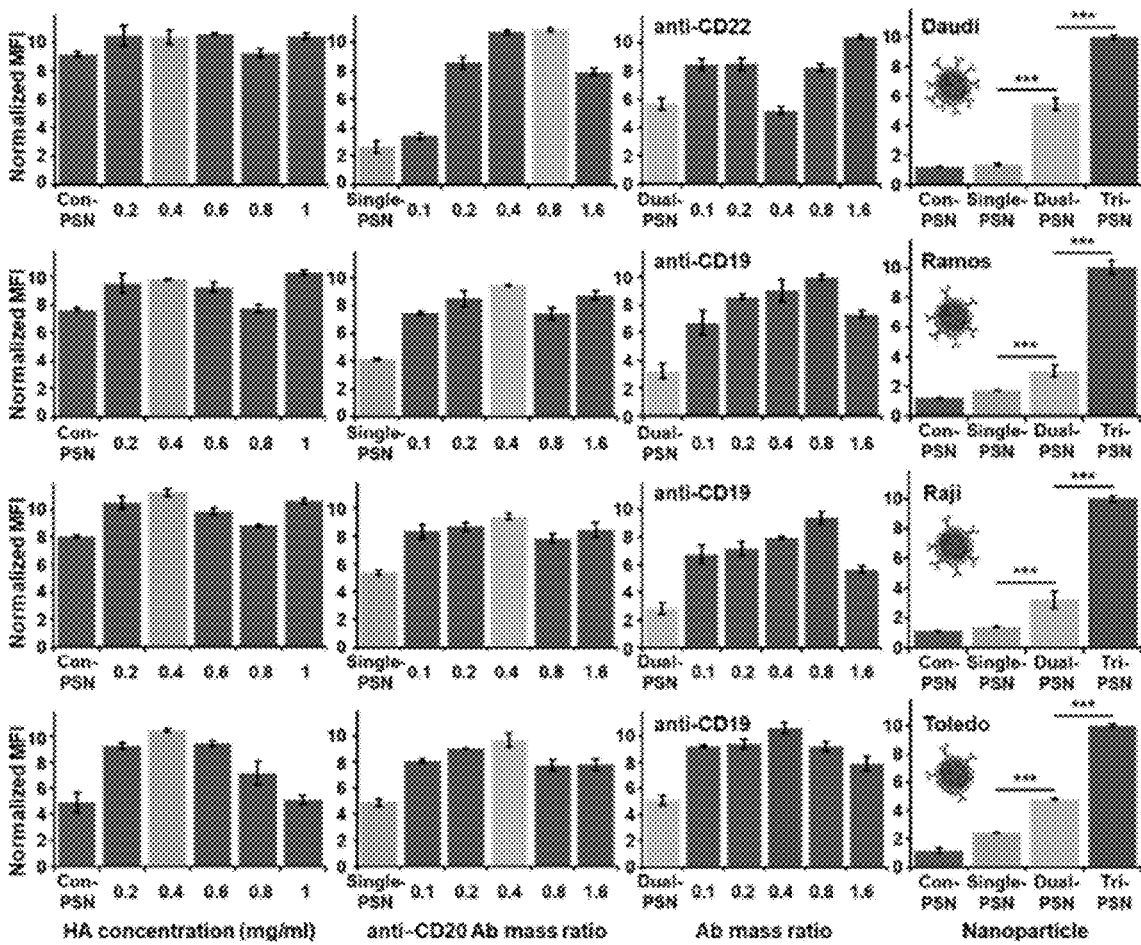
FIG. 10 relates to optimization of HA, anti-CD20, and anti-CD19/anti-CD22 antibody (Ab) ligand density on Tri-PSNs, and shows the results of flow cytometric analysis of Daudi, Raji, Ramos, and Toledo cells after treatment with Cy5.5-labeled PSNs with various HA concentrations and mass ratios of antibodies for the same concentration of siRNA (20 nM).

Their intracellular delivery to each NHL cell line was analyzed by flow cytometry to evaluate the optimized targeting conditions (FIG. 10). First, single-PSNs layered with 0.4 mg/mL HA showed the highest MFI as compared with those treated with other concentrations of HA and had 2.1-fold higher cellular uptake than Con-PSNs in Toledo cells. However, their fluorescence was relatively similar among the other NHL cell lines. This difference may result from variances in the level of the CD44 receptor in NHL cells.

Concerning the antibody/HA ratio, flow cytometry data suggested that anti-CD20-conjugated PSNs (dual-PSNs) had improved intracellular delivery only when the ratio of anti-CD20 antibody/HA was 0.8 and 0.4 in Daudi and other NHL cells, respectively.

Tri-PSNs showed further improved intracellular delivery when an additive antibody (anti-CD19 or anti-CD22) was introduced. In detail, a 1.6 mass ratio of anti-CD22 led to the highest intracellular delivery in Daudi cells, whereas a 0.8 mass ratio of anti-CD19 showed the highest intracellular delivery in Raji and Ramos cells. In the case of Toledo cells, a 0.4 mass ratio of anti-CD19 cells achieved the highest intracellular delivery. These results are associated with the steric hindrance between adjacent antibodies on the Tri-PSN, as the conjugation amount of the anti-CD19 antibody increased with an initial concentration similar to that used in a previously reported dual targeting nanoplatform.

Ultimately, Tri-PSNs that were optimized for Daudi, Raji, Ramos, and Toledo cells showed 8.4-, 9.1-, 8.1-, and 8.7-fold higher cellular uptake, respectively, than positively charged Con-PSNs, confirming that the introduction of multiple targeting moieties on the nanoparticles was successful. These drastic enhancements were expected to result from the enforced interactions between the nanoparticles and target cells due to the increased targeting moieties.

In addition, different optimal ratios of targeting moieties were required due to the expression of each receptor in NHL cells, which required a different density of functionalized targeting moieties on the surface of targeted nanoparticles, spatial arrangement of those ligands, and multiple ligand-receptor pairs for optimal interaction between the nanoparticles and the receptors on the cell surface. Overall, specific receptor-mediated endocytosis was facilitated as the multiple receptors targeted in the NHL cells were able to effectively interact with the nanoparticles, due to the number and density of targeting moieties, thereby resulting in significantly enhanced intracellular delivery.

2.6. In Vitro Cellular Uptake and Therapeutic Efficacy

Figure 11:
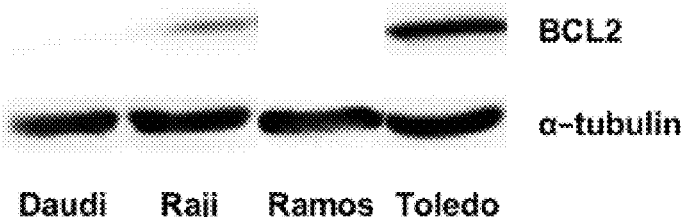
FIG. 11 shows basal BCL2 levels in Daudi, Raji, Ramos, and Toledo cells by western blot analysis.

For the investigation of the therapeutic efficacy of Tri-PSNs, the levels of BCL2 were evaluated. BCL2 was selected as the target gene, as the corresponding protein is overexpressed in some hematological malignancies and is related to pro-proliferative and anti-apoptotic signals in NHL cells. Therefore, the basal levels of BCL2 in the different NHL cell lines were investigated by western blotting (FIG. 11). Toledo cells were found to exhibit the highest BCL2 expression; thus, they were selected as a proof-of-concept model to assess the therapeutic efficacy of the PSNs.

Figure 12:
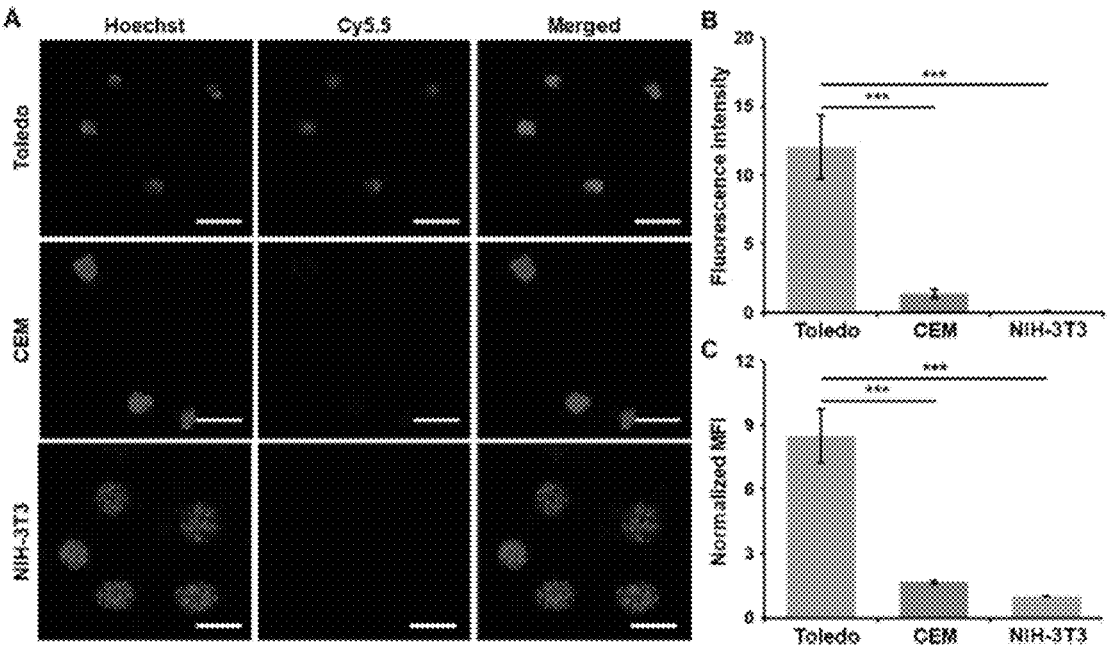
FIG. 12 relates to NHL-specific delivery of Tri-PSNs. (A) CLSM images of Toledo, CEM, and NIH-3T3 cells treated with Cy5.5-labeled Tri-PSNs (scale bars: 20 μm); (B) quantitative analysis of fluorescence intensity of the Tri-PSNs in Toledo, CEM, and NIH-3T3 cells based on CLSM images; and (C) normalized MFI based on flow cytometry analysis of Cy5.5-labeled Tri-PSNs-treated Toledo and CCRF-CEM cells.
Figure 13:
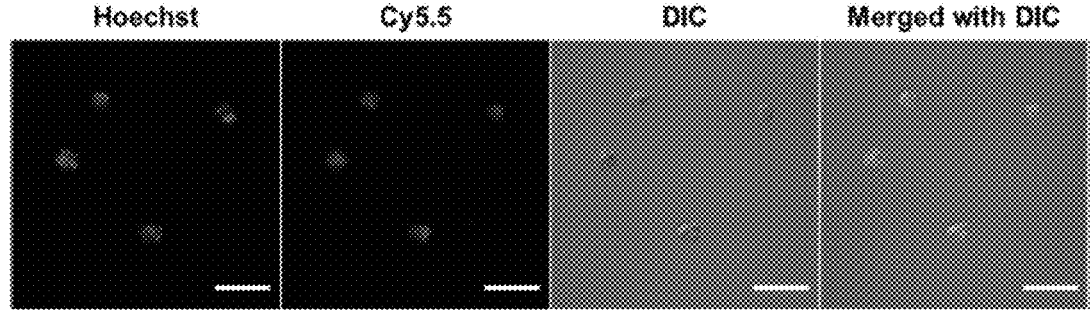
FIG. 13 shows fluorescence and differential interference contrast (DIC) images of Cy5.5-labeled Tri-PSNs-treated Toledo cells.

To further investigate NHL-specific intracellular delivery of Toledo-optimized Tri-PSNs, Toledo, CCRF-CEM, and NIH-3T3 cells were treated with Cy5.5-labeled Tri-PSNs, and the intracellular fluorescence was compared by CLSM and flow cytometry (FIGS. 12 and 13). The CLSM images showed significantly higher fluorescence in Tri-PSNs-treated Toledo cells than in CCRF-CEM and NIH-3T3 cells, which agreed with the quantitative flow cytometry data. Toledo-optimized Tri-PSNs showed 5.0- and 8.4-fold higher MFIs in Toledo cells than in CCRF-CEM and NIH-3T3 cells, respectively, indicating that the Tri-PSNs were successfully and specifically delivered to NHL cells.

Figure 14:
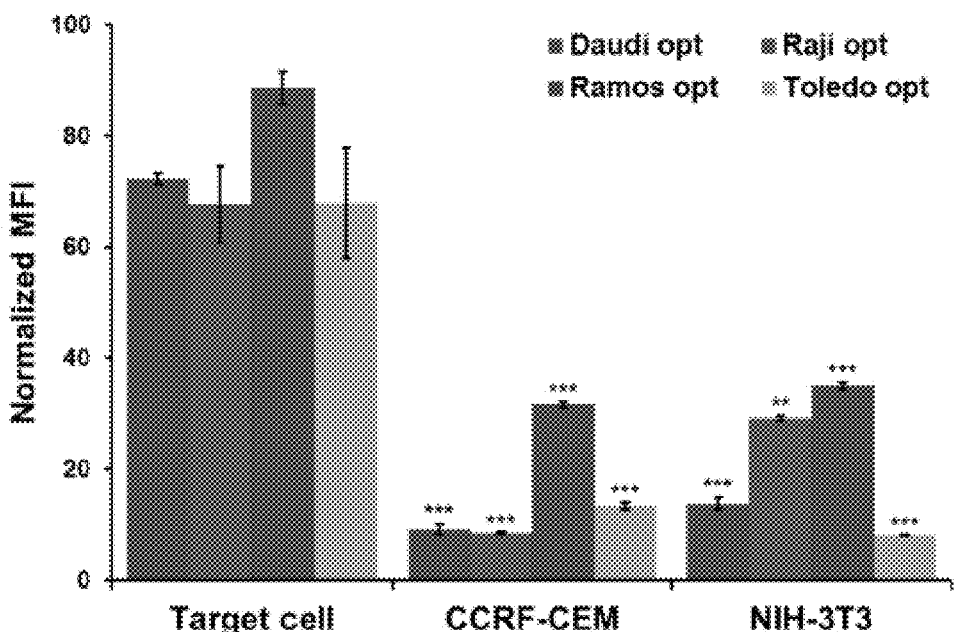
FIG. 14 shows the results of flow cytometry analysis of Daudi, Raji, Ramos, and Toledo cells after treatment with Cy5.5-labeled optimized PSNs.

Moreover, the intracellular delivery of other types of Tri-PSNs to CCRF-CEM and NIH-3T3 cells was evaluated to confirm the broad range of NHL cell-specific intracellular delivery of Tri-PSNs (FIG. 14). According to the flow cytometry results, all the Tri-PSNs showed significantly decreased or negligible cellular uptake in these cells, indicating the consistent applicability of the NHL cell-specific intracellular delivery strategy. The gene-silencing efficacy of the polymeric siRNA from the Tri-PSNs was assessed by quantification of BCL2 expression in Toledo cells by western blotting (FIG. 15A). Treatment with Tri-PSNs down-regulated BCL2 expression by 79.3% in Toledo cells. This high gene-silencing efficacy can be explained by the improved cellular delivery of the Tri-PSNs with multiple targeting moieties, which in turn resulted in endosomal escape of the polymeric siRNA, their decomplexation in the cytosol, and consequent structural cleavage of the targeted mRNA.

Furthermore, the antiproliferative effects of the Tri-PSNs were also evaluated by the alamarBlue assay after 72 h of incubation with Toledo cells (FIG. 15B). RNA therapeutic from Tri-PSNs inhibited Toledo cell proliferation in a dose-dependent manner. Moreover, Tri-PSNs at 100 nM siRNA inhibited Toledo cell proliferation by 67.5%. Notably, it induced approximately 10-fold higher BCL2 downregulation and cytotoxicity of Toledo cells than that induced by previously reported nanoplatforms for monomeric siRNA. 26 In contrast, Tri-PSNs exhibited negligible antiproliferative effects in nontargeted CCRF-CEM cells. Overall, these results indicate that Tri-PSNs successfully induce apoptosis-mediated inhibition of NHL cell proliferation without imparting intrinsic toxicity.

From the foregoing, it will be understood by those skilled in the art to which the present disclosure pertains that the present disclosure may be embodied in other specific forms without departing from the technical spirit or essential characteristics of the present disclosure. Therefore, it should be understood that the embodiments described above are illustrative in all aspects and not restrictive. Furthermore, the scope of the present disclosure should be defined by the appended claims rather than the detailed description, and it should be understood that all modifications or variations derived from the meanings and scope of the present disclosure and equivalents thereto fall within the scope of the present disclosure.

What is claimed is:

1. A lymphoma cell-specific drug delivery system for prevention or treatment of lymphoma, the drug delivery system being composed of a nanoparticle comprising:

a core containing a mixture of a prophylactic or therapeutic drug and poly-L-lysine;

a shell composed of hyaluronic acid layered on a surface of the core;

an anti-CD20 antibody conjugated to a surface of the shell; and an anti-CD19 antibody or anti-CD22 antibody conjugated to the surface of the shell, wherein a weight ratio of the anti-CD20 antibody to the hyaluronic acid in the nanoparticle is 0.3 to 1.0, wherein a weight ratio of the anti-CD19 antibody, if present, to the hyaluronic acid in the nanoparticle is 0.3 to 1.0, wherein a weight ratio of the anti-CD22 antibody, if present, to the hyaluronic acid in the nanoparticle is 1.5 to 1.7, wherein the anti-CD20 antibody and the anti-CD19 antibody, if present, have a mass ratio of 1:2, and wherein the anti-CD20 antibody and the anti-CD22 antibody, if present, have a mass ratio of 1:2.

2. The lymphoma cell-specific drug delivery system according to claim 1, wherein the prophylactic or therapeutic drug is an anticancer drug, an anticancer adjuvant agent, or an siRNA that inhibits expression of a target gene in lymphoma cells.

3. The lymphoma cell-specific drug delivery system according to claim 2, wherein the target gene in lymphoma cells is BCL2 gene.

4. The lymphoma cell-specific drug delivery system according to claim 1, wherein the lymphoma is Burkitt's lymphoma, diffuse large B-cell lymphoma (DLBCL), Hodgkin's lymphoma, or non-Hodgkin's lymphoma.

5. The lymphoma cell-specific drug delivery system according to claim 1, which has a zeta-potential of −20 to −22 mV in an environment of pH 6.3 to 6.5.

6. A method for producing the lymphoma cell-specific drug delivery system according to claim 1, the method comprising steps of:

synthesizing an siRNA that complementarily binds to a target gene in lymphoma cells;

synthesizing polymeric siRNA microparticles by mixing and incubating a ribonucleotide solution containing the siRNA, a buffer, a reducing agent, and a polymerase;

synthesizing concentrated polymeric siRNA nanoparticles by mixing a fluorophore-conjugated poly-L-lysine solution, a buffer, and the polymeric siRNA microparticles;

synthesizing hyaluronic acid-layered polymeric siRNA nanoparticles by mixing and incubating the concentrated polymeric siRNA nanoparticles with a hyaluronic acid solution and a tetrazine solution; and adding a trans-cyclooctene-NHS ester (TCO)-conjugated antibody to the hyaluronic acid-layered polymeric siRNA nanoparticles, thereby conjugating the antibody to surfaces of the nanoparticles.

7. The method according to claim 6, wherein a concentration of the hyaluronic acid solution is 0.3 to 0.5 mg/ml.

* * * * *